United States Patent [19]

Erickson et al.

[11] Patent Number: 5,245,896
[45] Date of Patent: Sep. 21, 1993

[54] QUICK-CHANGE TOOL HOLDER WITH CENTER HEIGHT ADJUSTMENT MECHANISM

[75] Inventors: Robert A. Erickson, Raleigh; James A. Oshnock, Garner, both of N.C.

[73] Assignee: Kennametal Inc., Latrobe, Pa.

[21] Appl. No.: 932,141

[22] Filed: Aug. 19, 1992

[51] Int. Cl.⁵ .................... B23B 29/04; B23B 29/20
[52] U.S. Cl. ................................. 82/160; 407/89
[58] Field of Search ............... 82/158, 160; 407/73, 407/76, 80, 81, 82, 83, 88, 89

[56] References Cited

U.S. PATENT DOCUMENTS

| | | | |
|---|---|---|---|
| 4,632,614 | 12/1986 | Rall et al. | 82/161 |
| 4,655,631 | 4/1987 | Mitchell | 82/160 |
| 4,682,521 | 7/1987 | Duenas | 82/158 |
| 4,692,069 | 9/1987 | Kieninger | 407/89 |
| 4,736,659 | 4/1988 | Erickson | 82/158 |
| 5,040,932 | 8/1991 | Oshnock | 409/234 |
| 5,090,280 | 2/1992 | Kosker | 82/158 |

*Primary Examiner*—William E. Terrell
*Attorney, Agent, or Firm*—James G. Porcelli

[57] ABSTRACT

A quick-change tool holder includes a center-height adjustment mechanism for adjusting the center height of the cutting tool. The quick-change tool holder includes a tool support member which is adapted to be mounted on a lathe turret or mounting block of a machine, a cutting head formed with a seat for receiving a cutting tool, and a clamping mechanism for clamping the cutting head to the support member. The tool support member includes an axial bore which receives a tubular shank of the cutting unit. The clamping mechanism is disposed within the axial bore and includes a pair of radially expandable locking elements to engage the tubular shank of the cutting unit. The clamping mechanism includes a key which engages with a corresponding keyway on the tubular shank for angularly locating the cutting unit. An adjustment mechanism is provided for rotating the clamping means about a longitudinal axis of the support member to change the angular location of the cutting unit. The center height of the cutting tool is determined by the angular location of the cutting unit.

13 Claims, 4 Drawing Sheets

QUICK-CHANGE TOOL HOLDER WITH CENTER HEIGHT ADJUSTMENT MECHANISM

BACKGROUND OF THE INVENTION

The present invention relates generally to quick-change tooling for metalworking operations, such as boring and turning, and more particularly to a method and apparatus for adjusting the center height of the cutting tool.

A quick-change tool holder typically includes two separate components—a tool support member and a cutting head. The tool support member is installed on the machine and the cutting head clamps to the support member. The tool support member will normally receive many different types of cutting heads which can be interchanged with one another relatively quickly. Thus, quick-change tooling greatly reduces set-up time when switching from one machine operation to another.

The drawback with quick-change tooling, however, is that it is more difficult to maintain proper center height adjustment of the cutting tool. Quick-change tooling requires a greater number of parts than conventional fixed tooling. Even when the parts are manufactured according to close tolerances, the cumulative effect of such tolerance can have a significant effect on center height adjustment. Improper center height adjustment may result in increased cutting forces in the tool which could significantly affect tool life. Other problems associated with improper center height adjustment include excessive chatter during machining operations, rough surface finish on the workpiece, and unacceptable variations in the size of the finished workpiece.

SUMMARY AND OBJECTS OF THE INVENTION

The present invention is a quick-change tool holder having means for adjusting the center height of the cutting tool. The tool holder includes a support member which is adapted to be mounted on a lathe turret or mounting block, a cutting head formed with a seat for receiving the cutting tool, and a clamping mechanism for clamping the cutting head to the support member.

The clamping mechanism utilizes a pair of locking balls which are driven into engagement with apertures formed in a tubular shank on the cutting head. The locking balls are driven into engagement with the tubular shank by a locking wedge which is actuated by a screw. The locking balls and the locking wedge are contained within a ball canister which is disposed in the axial bore of the support member. The ball canister includes a key which cooperates with a keyway on the tubular shank to angularly locate the cutting head.

Center height adjustment is achieved by rotating the ball canister about a longitudinal axis thereby altering the position of the cutting tool. Various methods may be used for rotating the ball canister. The disclosed embodiment utilizes a ball and screw arrangement. More particularly, the ball canister is formed with a pair of detents or recesses The detents are engaged by force transmitting balls, each of which is activated by a cup-point adjusting screw. The axis of the adjusting screws are offset with respect to the axis of the canister and provide counter balancing torque on the canister. The canister can be rotated in either direction to adjust the center height of the tool by loosening one screw and tightening the opposite screw.

Based on the forgoing, it is apparent that the primary objective of the present invention is to provide a quick-change tool holder having means for adjusting the center height of the cutting tool.

Another object of the present invention is to provide a quick-change tool holder wherein the effect of tolerances on center height adjustment are largely eliminated.

Yet another object of the present invention is to provide a center height adjustment mechanism which has sufficient load carrying capacity that is can maintain its position during machining operations.

Still another object of the present invention is to provide a quick-change tool holder having a center height adjustment mechanism which is relatively simple in construction and which can be produced economically.

Another object of the present invention is to provide a quick-change tool holder with a center height adjustment mechanism which will be relatively easy to use and which can be adjusted relatively quickly.

Other objects and advantages of the present invention will become apparent and obvious from a study of the following description and the accompanying drawings which are merely illustrative of such invention.

DETAILED DESCRIPTION OF THE DRAWINGS

DETAILED DESCRIPTION OF THE INVENTION

Figure 1:
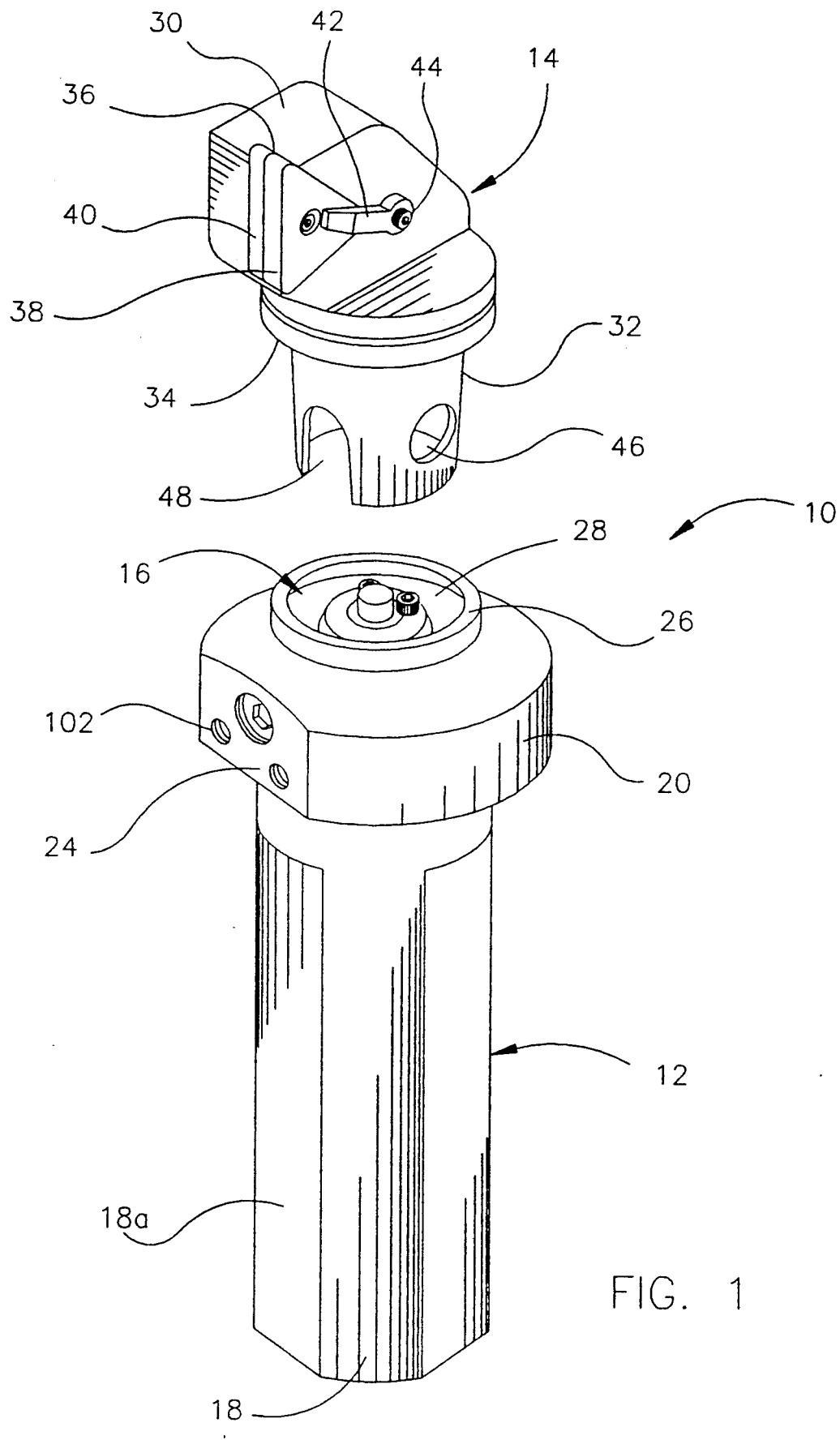
FIG. 1 is an exploded perspective view of one embodiment of the tool holder assembly of the present invention.
Figure 2:
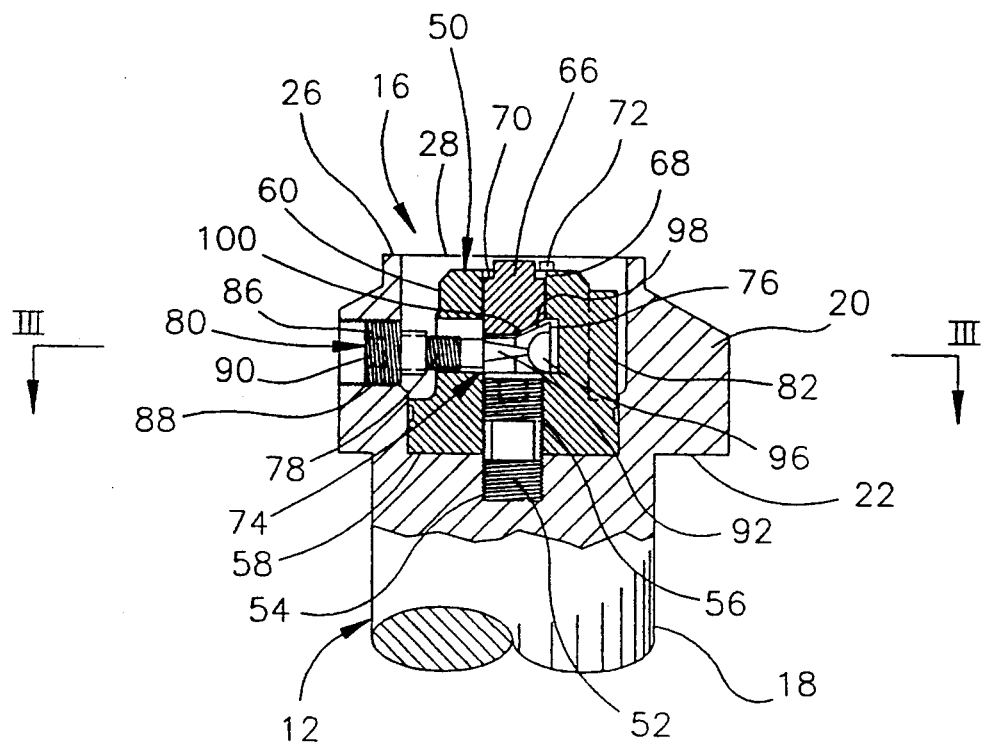
FIG. 2 is a partial section view of the tool support member taken along a medial plane of the support member.

Referring now to the drawings, and particularly to FIG. 1, the tool holder assembly of the present invention is shown therein and indicated generally by the numeral 10. The tool holder assembly includes a tool support member indicated generally at 12, a cutting head 14 adapted to receive and hold the cutting tool, and a clamping mechanism 16 for clamping the cutting head 14 to the support member 12.

The support member 12 includes a generally cylindrical shank 18 which is received in an axial bore formed in the turret or mounting block (not shown) of the machine. The shank has one or more flats 18a formed in the surface thereof which are engaged by set screws (not shown) to secure the support member 12 in the turret or mounting block. A flange 20 is formed adjacent the forward end of the support member 12. The flange 20 includes a rearwardly facing surface 22 which seats against the face of the turret or mounting block. A flat surface 24 is formed on one side of the flange 20. An axial bore 28 is formed in the forward end of the support member 12 and is surrounded by a forwardly facing seating surface 26. The axial bore 28 has a slightly frusto-conical configuration and is adapted to receive the cutting head 14 as will be hereinafter described.

Referring now to the cutting head 14, it includes a forward portion 30 and a rearwardly extending, tubular shank 32. A rearwardly facing abutment surface 34 is formed at the junction between the tubular shank 32 and the forward portion 30. The forward portion 30 is formed with a tool receiving pocket 36 adapted to receive a conventional cutting insert 38 and shim 40. The cutting insert 38 includes two converging cutting edges which meet to form a rounded cutting tip. The top of the cutting insert 38 is engaged by a clamping member 42 to secure the insert 38 and shim 40 in the tool receiving pocket 36. The clamping member 42 is secured to the forward portion by a clamp screw 44 which threads into a corresponding hole (not shown) in the top of the forward portion 30.

The tubular shank 32 is integrally formed with the forward portion 30 and is preferably machined from a single piece of steel. The shank 32 has a frusto-conical shape which matches the axial bore 28 of the support member 12. Two diametrically opposed apertures 46 perforate the tubular shank 32. The tubular shank 32 also includes two diametrically opposed key slots 48 which are disposed along a radial axis that is perpendicular to the axis of the apertures 46.

When mounting the cutting head 14 to the support member 12, the tubular shank 32 is received in the axial bore 28. The clamping mechanism 16 is disposed in the axial bore 28 for securing the cutting head 14 on the support member 12.

The clamping mechanism 16 includes a ball canister 50 which is secured in the axial bore 28 of the support member 12 by a double-ended screw 52. A first end of the double-ended screw 52 threads into a corresponding screw hole 54 in the bottom of the axial bore 28. The second end of the screw 52 threads into a corresponding screw hole 56 in the base 58 of the canister 50.

The ball canister 50 includes an upper portion 60 having a key 82 formed on its exterior which is sized to fit into one of the key slots 48 on the tubular shank 32 of the cutting unit 14. Two transverse passages 62 and 64 are formed in the canister 50 which extend perpendicularly to the longitudinal axis of the tool holder. A bump-off pin 66 is loosely mounted in a longitudinal passage 68 in the top of the ball canister 50. The bump-off pin 66 includes a shoulder 70 which is engaged by two small screws 72 to retain the bump-off pin 66 in the longitudinal passage 68.

An actuating member 74 is disposed in the first longitudinal passage 62 of the ball canister 50. The actuating member 74 includes a head portion 76 and a shank portion 78. The shank portion 78 is externally threaded. An actuating screw 80 provides means for reciprocally moving the actuating member 74. The actuating screw 80 includes an internally threaded bore 84 which engage the threads on the shank portion 78 of the actuating member 74. The actuating screw 80 also includes external threads 86 which are opposite to the threads in the threaded bore 84. The external threads 86 engage a threaded opening 88 in the support member 12. On the end of the actuating screw 80 which is accessible from the exterior of the support member 12, there is a hexagonal depression 90 which is adapted to be engaged by an Allen wrench.

The head portion 76 of the actuating member 74 includes a pair of ball driving ramps 92 on opposite sides thereof. The ball driving ramps 92 are adapted to engage locking balls 94 which are loosely received in the transverse passage 64. The ball driving ramps 92 decline inwardly as they extend away from the shank portion 78 until they join concave-spherical depressions 96. The actuating member 74 also includes an inclined surface 98 adapted to engage a corresponding surface 100 on the bottom of the bump-off pin 66.

Figure 3:
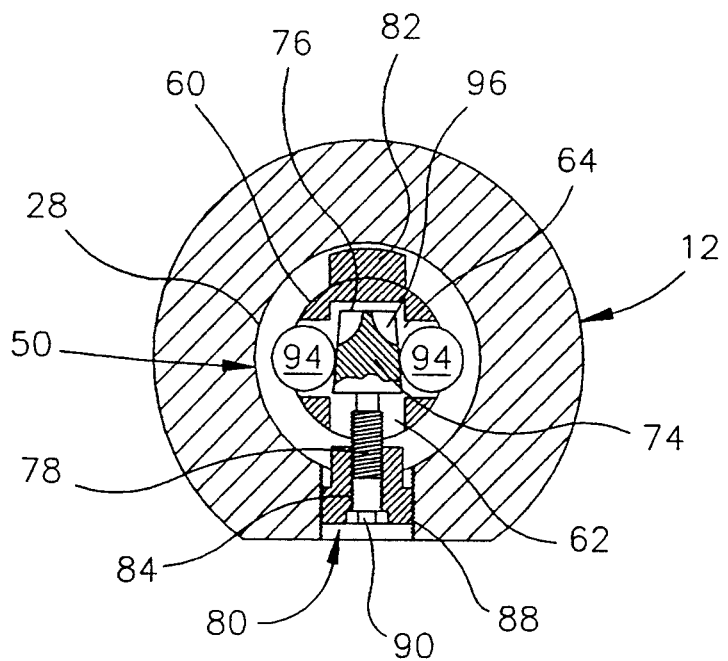
FIG. 3 is cross-section view of the tool support member taken through line III—III of FIG. 2.
Figure 4:
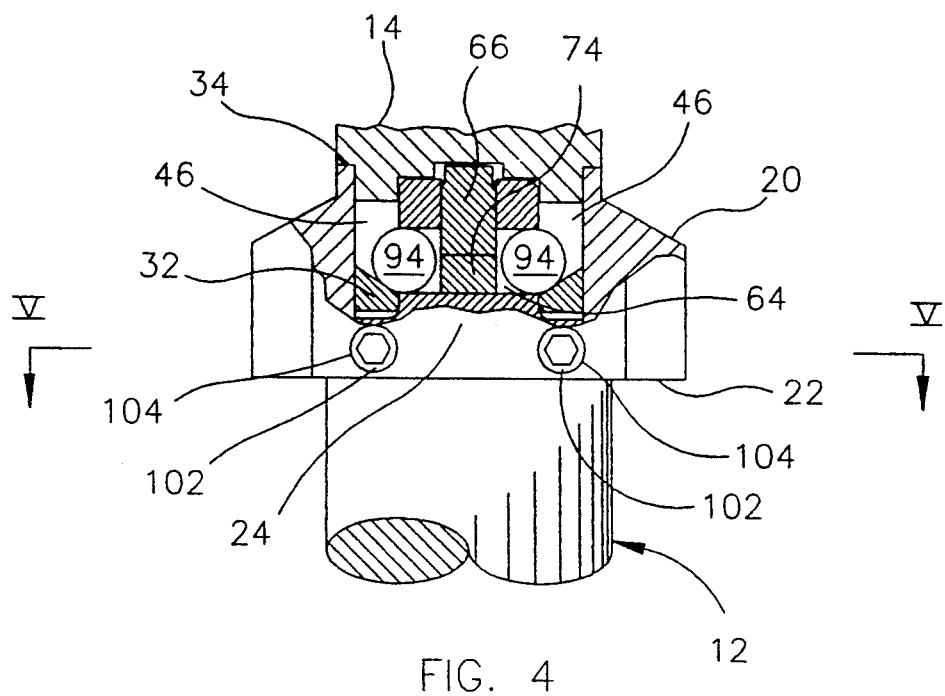
FIG. 4 is a front elevation view of the tool holder assembly with a portion shown in section.

It will be readily apparent from the foregoing description that when the actuating screw 80 is turned in a first direction, the actuating member 74 will be moved to displace the locking balls 94 from spherical depressions 96 and on to the ball driving ramps 92. The locking balls 94 are thus driven outwardly as best shown in FIGS. 3 and 4. When the actuating screw 80 is rotated in a second direction, the actuating member 74 is moved in a second direction to allow the locking balls 94 to roll back into the spherical depressions 96. At the same time, the inclined surface 98 on the actuating member 74 engages the corresponding inclined surface 100 on the bump-off pin 66 to push it upward. The bump-off pin 66, in turn, pushes upwardly against the cutting head 14 to separate the cutting head 14 from the support member 12.

In use, the cutting head 14 is mounted on the support member 12 by inserting the tubular shank 32 of the cutting head 14 into the axial bore 28 of the support member 12. After inserting the cutting head 14 into the support member 12, the actuating screw 80 is rotated in a first direction, normally clock-wise, to clamp the cutting head 14 to the support member 12. As already described, the rotation of the actuating screw 80 causes the actuating members 74 to urge the locking balls 94 radially outward into engagement with the apertures 46 in the tubular shank 32. As shown best in FIG. 4, the walls of the aperture 46 are slightly inclined so that the engagement of the locking balls 94 with the apertures 46 exerts a rearward force on the cutting head 14 and seats the abutment surface 34 against the seating surface 26 on the support member 12. Once the cutting head 14 is mounted on the support member 12, the angular location of the cutting head 14 is determined by the engagement of the key 82 on the ball canister 50 with the corresponding key slot 48 in the tubular shank 32 of the cutting head 14. Ideally, the key and key slot 48 should always locate the cutting head 14 so that proper center height adjustment is obtained. In actual practice, however, proper center height adjustment cannot be assured due to the number of components and the tolerances to which they are made. The present invention attempts to eliminate, to a large extent, the effect of these tolerances on center height adjustment by providing means for adjusting the center height of the cutting tool.

Figure 5:
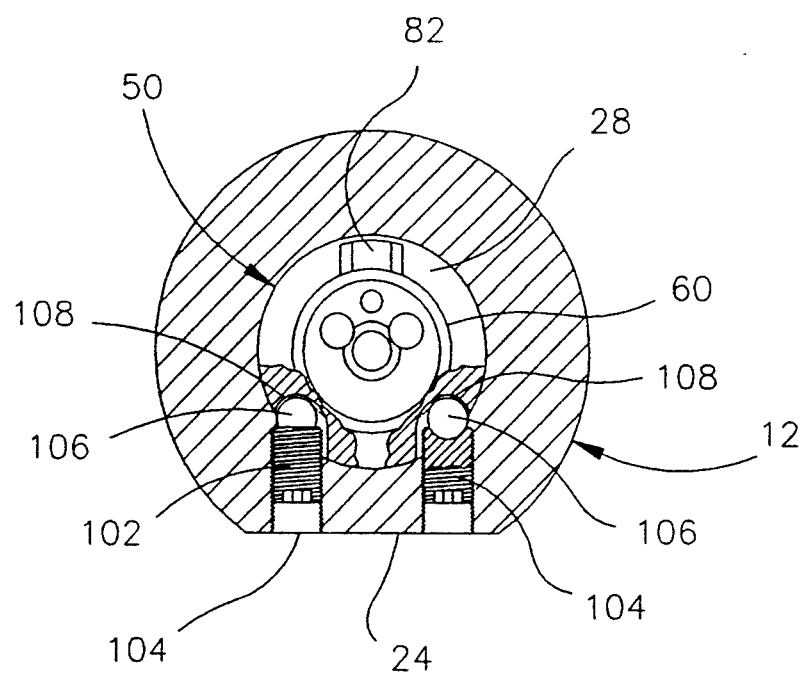
FIG. 5 is a cross-section view of the tool support member taken through line V—V of FIG. 4.
Figure 6:
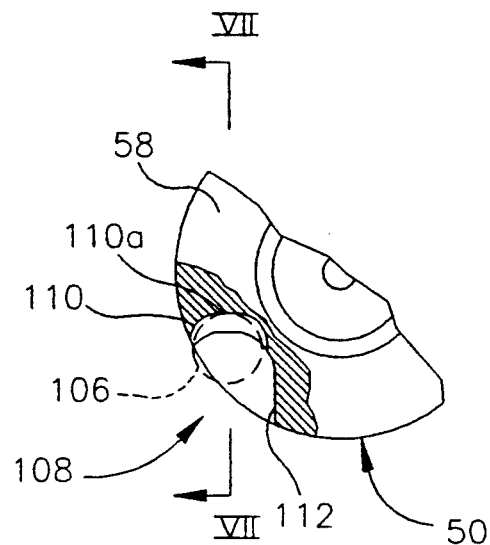
FIG. 6 is a partial top plan view of the ball canister with a portion shown in section to illustrate the recess.
Figure 7:
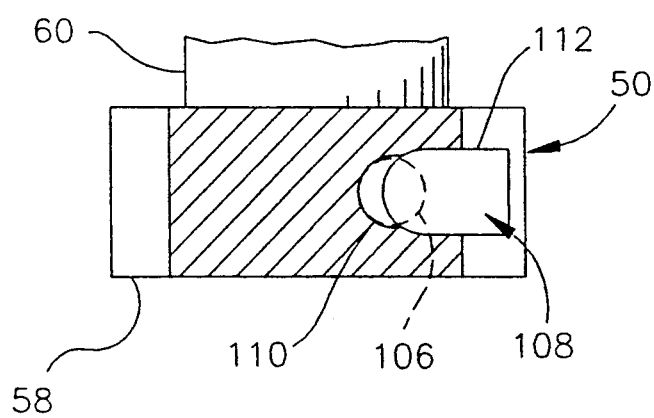
FIG. 7 is a section view of the ball canister taken through line VII—VII of FIG. 6.

Referring now to FIGS. 5–7, the center height adjustment means comprises a pair of cup-point adjusting screws 102 which exert counter balancing torque on the ball canister 50. The adjusting screws 102 are threadably engaged in adjusting-screw holes 104 in the flange 20 of the support member 12. Each adjusting screw 102 engages a force-transmitting element 106 which in turn engages a recess 108 in the base 58 of the ball canister 50. The recess 108 includes a seating portion 110 in which the force transmitting element 106 makes contact, and a clearance portion 112. The seating portion 110 is formed with a ball nose end mill whose diameter is roughly equal to the diameter of the force transmitting element 106. The clearance portion 112 is formed with a ball nose end mill having a slightly larger diameter.

As best shown in FIG. 6, the seating portion 110 of the recess 108 includes a flat portion 110a which is formed by moving the end mill laterally in a horizontal plane. The seating portion 110 remains generally circular in the view shown in FIG. 7. This configuration permits the force transmitting element 106 to make line contact with the seating portion 110 throughout the range of adjustment of the canister 50. The force transmitting element 106 also makes line contact with the cup-point adjustment screw 102. The line contact is important in giving the adjustment mechanism sufficient torque-carrying capacity to resist movement during machining operations.

To adjust the center height of the cutting tool, a first adjusting screw 102 is loosened and the second adjusting screw 102 is tightened to rotate the ball canister 50. When the desired position is attained, the first adjusting screw 102 is then retightened to lock the ball canister 50 in the adjusted position. The rotation of the ball canister 50 realigns the key 82, which in turn, causes the angular position of the cutting unit 14 to be changed. The center height of the cutting tool is determined by the angular location of the cutting unit 14.

Based on the foregoing, it is apparent that the center height adjustment mechanism provides an easy and convenient method for adjusting the center height of the cutting tool. By adjusting the center height, the forces on the cutting tool can be reduced, chatter can be eliminated, and a better surface finish on the workpiece can be obtained.

The present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced therein.

What is claimed is:

1. A quick-change tool holder having center-height adjustment means comprising:
   (a) a cutting unit including a rearwardly extending shank and a tool-receiving pocket for receiving and holding a cutting tool;
   (b) a tool support member having an axial bore for receiving the shank of the cutting unit;
   (c) clamping means disposed within said axial bore in the support member and including a locking element movable from an engaged position to a disengaged position for releasibly securing the cutting unit to the support member;
   (d) said clamping means including means for angularly locating the cutting unit;
   (e) center-height adjusting means including means for rotating the clamping means about a longitudinal axis of the support member between a plurality of angular locations; and
   (f) means for securing the clamping means in any one of said plurality of angular locations.

2. The tool holder according to claim 1 wherein the adjusting means includes at least one adjusting screw threadably engaged in an adjusting screw hole in the support member and engageable with the clamping means to rotate the clamping means about the longitudinal axis.

3. The tool holder according to claim 2 further including a force-transmitting element disposed between the adjusting screw and the clamping means for transmitting the force of the adjusting screw to the clamping means.

4. The tool holder according to claim 3 wherein the adjusting screw is a cup-point screw and the force-transmitting element is spherical.

5. The tool holder according to claim 2 wherein the adjusting means comprises a pair of adjusting screws threadably engaged in corresponding adjusting screw holes in the support member, and wherein said pair of adjusting screws apply opposing rotational forces to the clamping means.

6. The tool holder according to claim 1 wherein the locating means comprises a keyway formed in the shank of the cutting unit and a matching key formed on the clamping means.

7. A quick-change tool holder having center-height adjustment means comprising:
   (a) a cutting unit for receiving and holding a cutting tool and including a rearwardly extending tubular shank;
   (b) a tool support member having an axial bore for receiving the tubular shank of the cutting unit;
   (c) a clamping unit disposed within the axial bore of the support member for releasably securing the cutting unit to the support member, said clamping means including:
      (1) a canister rotatably mounted in the axial bore of the support member and insertable into the tubular shank of the cutting unit, said canister being rotatable between a plurality of angular locations;
      (2) at least one locking element disposed in the canister and movable between an engaged position for engaging the tubular shank to secure the cutting unit to the support member and a disengaged position for releasing the cutting unit;
      (3) actuating means for urging the locking element to the engaged position;
      (4) locating means for angularly locating the cutting unit with respect to the canister; and
   (d) center height adjustment means for adjusting the center height of the cutting tool, said center height adjusting means including a pair of adjusting screws threadably engaged in respective adjusting screw holes in the support member for rotating the canister about its longitudinal axis to a selected angular location, and for securing the canister in any one of said angular locations.

8. The quick-change tool holder according to claim 6 wherein the locating means comprises a keyway formed in the tubular shank of the cutting unit and a matching key formed on the canister of the clamping means which is insertable into the keyway in the tubular shank.

9. The quick-change tool holder according to claim 6 wherein the center height adjustment means further comprises a pair of force transmitting elements for transmitting the rotational force of the adjusting screws to the canister.

10. The quick-change tool holder according to claim 9 wherein the force transmitting elements have a generally spherical configuration.

11. The quick-change tool holder according to claim 10 wherein the canister includes a pair of concave recesses which are engaged by the spherical force transmitting elements.

12. The quick-change tool holder according to claim 11 wherein the force transmitting elements make line contact with the concave recesses in the canister.

13. The quick-change tool holder according to claim 9 wherein the adjusting screws are cup-point screws and make line contact with the force transmitting elements.

* * * * *